United States Patent
Jaafari et al.

(10) Patent No.: US 10,123,973 B2
(45) Date of Patent: Nov. 13, 2018

(54) LIPOSOME COMPOSITION FOR CANCER TREATMENT

(71) Applicants: Mahmoud Reza Jaafari, Mashhad (IR); Fatemeh Gheybi, Mashhad (IR); Seyed Mahdi Rezayat Sorkhabadi, Tehran (IR)

(72) Inventors: Mahmoud Reza Jaafari, Mashhad (IR); Fatemeh Gheybi, Mashhad (IR); Seyed Mahdi Rezayat Sorkhabadi, Tehran (IR)

(73) Assignees: MASHHAD UNIVERSITY OF MEDICAL SCIENCE, Mashhad (IR); TEHRAN UNIVERSITY OF MEDICAL SCIENCE, Tehran (IR); Mahmoud Reza Jaafari, Mashhad (IR); Fatemeh Gheybi, Mashhad (IR); Seyed Mahdi Rezayat Sorkhabadi, Mashhad (IR)

( * ) Notice: Subject to any disclaimer, the term of this patent is extended or adjusted under 35 U.S.C. 154(b) by 121 days.

(21) Appl. No.: 15/130,116

(22) Filed: Apr. 15, 2016

(65) Prior Publication Data

US 2016/0228365 A1  Aug. 11, 2016

Related U.S. Application Data

(60) Provisional application No. 62/173,941, filed on Jun. 11, 2015.

(51) Int. Cl.
| | | |
|---|---|---|
| *A61K 9/127* | (2006.01) | |
| *A61K 31/357* | (2006.01) | |
| *A61K 47/48* | (2006.01) | |

(52) U.S. Cl.
CPC .......... *A61K 9/1271* (2013.01); *A61K 31/357* (2013.01); *A61K 47/48053* (2013.01); *A61K 47/48215* (2013.01); *A61K 47/48815* (2013.01)

(58) Field of Classification Search
CPC ............ A61K 49/0043; A61K 49/0054; A61K 49/0056; A61K 49/0058; A61K 49/0091; A61K 49/223; A61K 51/1255; A61K 49/0002; A61K 49/0047; A61K 51/127; A61K 2300/00; A61K 47/48038; A61K 47/48238; A61K 47/48869; A61K 47/542; A61K 47/62; A61K 47/6925; A61K 51/065; A61K 31/7036; A61K 33/14; A61K 51/088; A61K 31/357; A61K 9/1271; A61K 2039/53; A61K 2039/542; A61K 2039/55555; A61K 31/07; A61K 39/12; A61K 39/145; A61K 39/39; A61K 47/02; A61K 47/24; A61K 27/18053; A61K 47/28215; A61K 47/48815; A61K 9/1274

See application file for complete search history.

(56) References Cited

U.S. PATENT DOCUMENTS

| | | | |
|---|---|---|---|
| 2002/0146450 A1* | 10/2002 | Slater | A61K 9/1271 |
| | | | 424/450 |
| 2004/0071768 A1* | 4/2004 | Sarris | A61K 9/127 |
| | | | 424/450 |
| 2007/0087047 A1 | 4/2007 | Zalipsky et al. | |
| 2008/0031883 A1* | 2/2008 | Torchilin | A61K 31/50 |
| | | | 424/152.1 |
| 2010/0158928 A1* | 6/2010 | Stoermer | C07D 471/04 |
| | | | 424/178.1 |
| 2011/0117216 A1* | 5/2011 | Velasco Diez | A61K 31/05 |
| | | | 424/725 |

OTHER PUBLICATIONS

Cheung C, Silibinin—a promising new treatment for cancer, Anti cancer agents in medicinal chemistry, 2010, 10, 186-195.*

Lei Zhou, Endosomal pH-activatable poly (ethylene oxide)-graft-doxorubicin prodrugs: synthesis, drug release, and biodistribution in tumor-bearing mice, Biomacromolecules, 2011, vol. 12, Issue 5, pp. 1460-1467.

Amit A. Kale, Enhanced transfection of tumor cells in vivo using "Smart" pH-sensitive TAT-modified pegylated liposomes, Journal of Drug Targeting, 2007, vol. 15, Issue 7-8, pp. 538-545.

Paula C.A. Rodrigues, Acid-sensitive polyethylene glycol conjugates of doxorubicin: preparation, in vitro efficacy and intracellular distribution, Bioorganic & Medicinal Chemistry, Nov. 1999, vol. 7, Issue 11, pp. 2517-2524.

Imran Ahmad, Antibody-mediated specific binding and cytotoxicity of liposome-entrapped doxorubicin to lung cancer cells in vitro, Cancer research, Sep. 1, 1992, vol. 52, Issue 17, pp. 4817-4820.

* cited by examiner

*Primary Examiner* — Nannette Holloman
(74) *Attorney, Agent, or Firm* — NovoTechIP International PLLC

(57) ABSTRACT

Disclosed is a liposomal composition for treatment of cancer, which includes at least one PEG-Phospholipid conjugated molecule, cholesterol, and at least one phospholipid.

17 Claims, 2 Drawing Sheets

LIPOSOME COMPOSITION FOR CANCER TREATMENT

CROSS REFERENCE TO RELATED APPLICATION

This application claims the benefit of priority from U.S. Provisional Patent Application Ser. No. 62/173,941, filed on Jun. 11, 2015, and entitled "POLY ETHYLENE GLYCOL-PHOSPHOLIPID CONJUGATED MOLECULES WITH CYTOTOXIC EFFECTS, SYNTHESIZING THE SAME AND USE THEREOF IN CANCER TREATMENT" which is incorporated by reference herein in its entirety.

TECHNICAL FIELD

The present application generally relates to polyethylene glycol and phospholipid conjugated molecules, more particularly to a method for synthesizing polyethylene glycol-phospholipid conjugated molecules, which can possess cytotoxic effects among other potential effects and activities.

BACKGROUND

One of the major causes of death in the world is cancer. It is estimated that cancer will potentially lead to 12 million deaths in 2030. Radiotherapy, chemotherapy, and surgery are conventional cancer treatments known in the art. However, most current treatments cannot completely cure the patients, and therefore, many challenges still remain. Reasons for failure of known, conventional cancer treatments include high non-selective cytotoxicity, low response rates in solid tumors, adverse effects, and development of resistance.

Therefore, there is a need in the art for the development of new therapeutic agents that selectively act on the target tissue without side effects.

SUMMARY

The following brief summary is not intended to include all features and aspects of the present application, nor does it imply that the application must include all features and aspects discussed in this summary.

In one general aspect, the present application describes a liposomal composition for treatment of cancer, which includes: at least one PEG-Phospholipid conjugated molecule, cholesterol, and a phospholipid.

In a further general aspect, the present invention describes a liposome composition, which includes: at least one anti-cancer drug, at least one PEG-containing heterobifunctional cross-linker, cholesterol, and a phospholipid.

The above general aspects may include one or more of the following features. The PEG-phospholipid conjugated molecule can have cytotoxicity that is selective to tumor cells, in other words, a tumor cell specific cytotoxic agent. The PEG-phospholipid conjugated molecule can include: polyethylene glycol, at least one thiolated phospholipid, and at least one linker. The PEG-phospholipid conjugated molecule can form hydrazone bond in the composition. The molar percent of the PEG-phospholipid conjugated molecule in the liposomal composition can range from about 3 to about 6 percent.

In some implementations, the thiolated phospholipid in the PEG-phospholipid conjugated molecule can be selected from the group consisting of dipalmitoyl phosphatidyl thioethanol, distearoyl phosphatidyl thioethanol, dioleoyl phosphatidyl thioethanol, Dimyristoyl-phosphatidyl thioethanol, and combinations thereof.

According to some implementations, the linker in the PEG-phospholipid conjugated molecule can be selected from the group consisting of 4-(maleimidomethyl) cyclohexane-1-carboxyl-hydrazide, trifluoroacetic acid (SMCC-Hydrazide), 3-N-Maleimidobenzohydrazide-HCL, 4-N-Maleimidobenzohydrazide-HCl, and 4-(2-N-Maleimido) methyl benzohydrazide-HCl.

In some implementations of the present application, the polyethylene glycol in the PEG-phospholipid conjugated molecule can have a molecular weight of about 500 Dalton to about 7000 Dalton In some implementations, the phospholipid can be selected from the group consisting of egg yolk phosphatidylcholine (EPC), soybean phosphatidylcholine, dipalmitoylphosphatidylcholine (DPPC), dimyristoylphosphatidylcholine (DMPC), distearoylphosphatidylcholine (DSPC), dioleoylphosphatidylcholine (DOPC) egg yolk phosphatidylethanolamine, dipalmitoylphosphatidylethanolamine, and combinations thereof.

According to one implementation, the molar ratio of Phospholipid:cholesterol:PEG-phospholipid conjugated molecule can range from about 20:3:1 to about 22:6:2.

According to some implementations, the anticancer drug can be selected from the group consisting of herbal drugs, chemotherapeutic agents, and combinations thereof. According to further implementations, the anticancer drug can be selected from the group consisting of Epigallocatechin-3-gallate (EGCG), soy isoflavones, Isoflavones genistein, daidzein, Coumarins, flavonoids, silibinin, polyphenols, baicalin, lycopenes, Vincristine, doxorubicin, cisplatin, 5-fluorouracil, Methotrexate, Cyclophosphamide, mustine, prednisolone, epirubicin, folinic acid, oxaliplatin, etoposide, bleomycin, and combinations thereof.

In one implementation, the molar ratio of phospholipid:cholesterol:anticancer drug:PEG-phospholipid conjugated molecule can range from about 20:5:3:1 to about 22:6:6:2.

Methods are disclosed, including methods directed to producing PEG-phospholipid conjugated molecules. Example operations according to various aspects of such methods can include synthesizing a hydrazide activated polyethylene glycol (PEG), and synthesizing PEG-phospholipid conjugated molecules, comprising reacting a phospholipid with the hydrazide activated PEG.

In an aspect, reacting the phospholipid with the hydrazide activated PEG produces mPEG2000-HZ-PE conjugates as the phospholipid conjugated molecules.

Additional methods are disclosed, including methods directed to preparation of a liposomal composition for treatment of cancer. Example operations according to various aspects of such methods can include synthesizing a hydrazide activated PEG, and synthesizing mPEG2000-HZ-PE conjugates, comprising reacting a phospholipid with the hydrazide activated PEG. According to one or more aspects, example operations can also include producing an empty liposome, using a phospholipid, the mPEG2000-HZ-PE conjugates and cholesterol, and loading the empty liposome with at least one anti-cancer drug, to produce the liposomal composition. In an aspect, loading the empty liposome with at least one anti-cancer drug can include loading the empty liposome with an herbal antic-cancer drug, a conventional anti-cancer drug, or both.

According to additional aspects, the phospholipid is a first phospholipid, and example operations can further include preparing a control liposomal composition. Example operations can include synthesizing a second phospholipid, using an aromatic ketone, synthesizing a PEG, and synthesizing mPEG2000-DSPE conjugate molecules, comprising reacting the second phospholipid with the PEG. According to one or more aspects, example operations can also include producing a control empty liposome, using the second phospholipid, the mPEG2000-DSPE conjugate molecules, and cholesterol, and loading the control empty liposome with the at least one anti-cancer drug, to produce the control liposomal composition.

BRIEF DESCRIPTION OF THE DRAWINGS

This application will be understood more clearly from the following description and the accompanying figures. These figures are given purely by way of an indication and in no way restrict the scope of the application. Of these figures.

DETAILED DESCRIPTION

Figure 1:
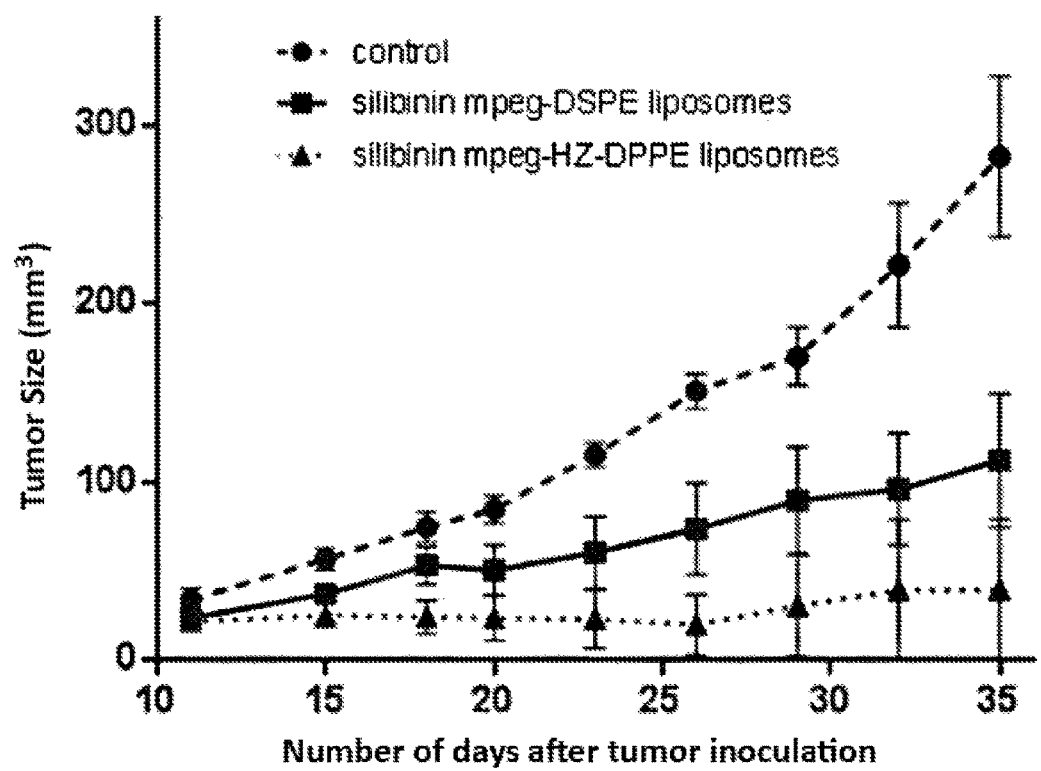
FIG. 1. Illustrates the results of tumor size monitoring tests in female BALB/c mice bearing 4T1 breast tumor treated by mPEG-HZ PE liposomal composition according to one or more aspects of this disclosure.

The following detailed description is presented to enable persons of ordinary skill in the art to make and use the teachings of the instant application. For purposes of explanation, specific examples are described to assist ones of skill in the art in readily understanding the concepts disclosed in the present application. However, it will be apparent to one skilled in the art that these specific details are not required to practice the teachings of the instant application. Descriptions of specific applications are provided only as representative examples. Various modifications to the described implementations will be readily apparent to one skilled in the art upon reading this disclosure, and the general principles defined herein may be applied to other implementations and applications without departing from the scope of the present application. The present application is not intended to be limited to the implementations shown, but is to be accorded the widest possible scope consistent with the principles and features disclosed herein.

A liposomal composition is introduced in the present disclosure that can be used, for example, for cancer treatment. The liposomal composition can include at least one PEG-Phospholipid conjugated molecule, cholesterol, and at least one phospholipid. A method is described for the synthesis of the PEG-Phospholipid conjugated molecule, which can possess tumor-specific cytotoxicity, and therefore, can be used in cancer treatment.

Heterobifunctional cross-linkers have two distinct reactive groups forming hydrazone bonds. In general, a hydrazone bond is formed by the reaction between hydrazines/hydrazides of one cross-linker with aldehydes and ketones group of another cross-linker in a solvent such as ethanol, methanol, tetrahydrofuran, butanol, glacial acetic acid or ethanol-glacial acetic acid, or combinations of such solvents. The conjugated molecules possess an —NHN═CH— and O═C—NH—N═CH moiety, which have a wide range of pharmacological properties in the development of novel compounds. The conjugated molecules have various biological activities, such as anti-inflammatory, anticonvulsant, analgesic, antidepressant, antiplatelet, antimycobacterial, antimalarial, antimicrobial, and anticancer activities. Conjugation via at least two cross-linkers, namely, uccinimidyl 4-(maleimidomethyl) cyclohexane-1-carboxyl-hydrazide, trifluoroacetic acid (SMCC-Hydrazide), and 4-Acetyl phenyl maleimide causes a hydrazone bond formation. The resulting molecules possess an O═C—NH—N═CH moiety.

The synthesized heterobifunctional cross-linkers (as PEG-Phospholipid conjugated molecule in present disclosure) can be used in various drug delivery systems with different platforms. In addition, the conjugated molecule can be accompanied by other drugs, to provide combination therapy. In another general aspect of the present application, a liposomal composition containing the polyethylene glycol-phospholipid conjugated molecule (PEG-Phospholipid conjugated molecules), which have tumor-specific cytotoxic effects, is disclosed.

In one implementation, at least one antitumor drug is loaded to the prepared liposomal composition. The tumor cell-specific cytotoxic effects of the prepared composition are confirmed via in-vivo and in-vitro studies. Various antitumor drugs can be applied in this combination therapy, including herbal drugs such as Epigallocatechin-3-gallate (EGCG), soy isoflavones, Isoflavones genistein and daidzein, Coumarins, flavonoids and polyphenols, baicalin, or lycopenes or conventional chemotherapy drugs such as Vincristine, doxorubicin, cisplatin, 5-fluorouracil, Methotrexate, Cyclophosphamide, mustine, prednisolone, epirubicin, folinic acid, oxaliplatin, etoposide, or bleomycin, and can include any combination of the herbal drugs, any combination of the conventional chemotherapy drugs, and any one or more among the herbal drugs in combination with any one or more among the conventional chemotherapy drugs. In one implementation of the present application, silibinin as an herbal drug can be used as the antitumor drug loaded to the prepared liposomal composition.

The following examples represent methods and techniques for carrying out aspects of the present application. It should be understood that numerous modifications can be made without departing from the intended scope of the disclosure.

Example 1

Synthesis of mPEG2000-HZ-PE Conjugates

One example method for synthesizing the mPEG2000-HZ-PE according to this application can comprise: first, synthesizing an aromatic ketone-derivatized phospholipid; second, synthesizing an acyl hydrazide-activated PEG; and finally, reacting the synthesized ketone-derivatized phospholipid with the hydrazide-activated PEG to obtain mPEG2000-HZ-PE conjugate.

Synthesis of an Aromatic Ketone-Derivatized Phospholipid

In one example, 27 mmol of phosphatidylthioethanol (DPPE-SH) was reacted with 40 micromoles of 4-acetyl phenyl maleimide, for four hours with constant stirring under inert atmosphere of argon in PBS. The product was then freeze dried. After dissolving the residue in chloroform: methanol (in ratio of about 9:1 by volume), the product was separated on a silica gel column using chloroform:methanol mobile phase (in ratio of about 9:1 by volume). The fractions containing the product were then identified by Thin Layer Choromatography (TLC) analysis. The fractions were collected and finally concentrated. Aromatic ketone-activated phospholipid was stored in a chloroform solution at 80° C.

Synthesis of Acyl Hydrazide-Activated PEG

For synthesizing acyl hydrazide-activated PEG, first, mPEG-SH (MW 2000) was reacted with 2 M excess of SMCC-Hydrazide in the presence of triethylamine for 8 hours in dry chloroform. Chloroform was evaporated under vacuum using a rotary evaporator, and the residue was dissolved in water. The PEG-hydrazide derivative was then separated and purified to obtain acyl hydrazide-activated PEG, using size exclusion gel chromatography. The exclusion gel chromatography used Sephadex G25m media. The product was freeze-dried and stored as a chloroform solution, for example at −80° C.

The Reaction Between Aromatic Ketone-Derivatized Lipid and Hydrazide Activated PEG Aromatic ketone-derivatized phospholipid was reacted with 1.5 M excess of hydrazide activated PEG derivative for approximately 48 hours under constant stirring, at 45° C. in chloroform, which produced mPEG2000-HZ-PE conjugate. The mPEG2000-HZ-PE conjugate was separated by size exclusion gel chromatography, using Sepharose-CL6B media.

Example 2

Preparation of Liposomes

Liposomes were prepared with phospholipids such as Dipalmitoylphosphatidylcholine (DPPC), cholesterol and mPEG2000-HZ-PE with a molar ratio of, for example, about 20:3:1 to about 22:6:2. In some implementations, the molar ratio can be about 21:5.6:1.4.

To compare the tumor cell-specific cytotoxic effects of the prepared liposome, another liposomal composition was prepared with the same molar ratio but using mPEG2000-DSPE instead of mPEG2000-HZ-PE. These empty liposomes were different only in containing mPEG2000-DSPE or mPEG2000-HZ-PE conjugates. The abovementioned liposomes were prepared using lipid film hydration and extrusion methods. In brief, the lipids were dissolved in an organic solvent. The example organic solvent was chloroform. Then, to form a thin layer lipid film, the organic solvent was removed by rotary evaporation. For complete removal of the organic solvents, the lipid film was freeze-dried. Then the lipid film was hydrated and dispersed in HEPES 10 mM containing 10% sucrose (pH 7), using a vortex at 50° C. The resulting multilamellar vesicles (MLVs) were then downsized by extrusion through stacked polycarbonate filters with a mini-extruder apparatus. Specific stacked polycarbonate filters were 200 nm and 100 nm polycarbonate filters. The particle size (Z-average), charge (Zeta potential), and poly dispersity index (PDI) of the liposomes were determined, using a particle size analyzer.

Example 3

Preparation of mPEG2000-DSPE and mPEG2000-HZ-PE Liposomes Loaded by Silibinin

Silibinin is one among herbal drugs that can be loaded into the prepared liposome composition pursuant to teachings of the present application to obtain drug-loaded liposomes. Silibinin-loaded liposomes were prepared using lipid film hydration and extrusion methods. In brief, Dipalmitoylphosphatidylcholine (DPPC) as a phospholipid, cholesterol, silibinin and mPEG2000-HZ-PE or mPEG2000-DSPE at molar ratios of about 21:5.6:3:1.55 was prepared. The phrase "mPEG2000-HZ-PE or mPEG2000-DSPE" in this context means that some silibinin-loaded liposomes were prepared to include mPEG2000-HZ-PE and some were prepared to include mPEG2000-DSPE.

Silibinin-loaded liposomes resulting from the above-summarized process differed only in that some possessed mPEG2000-DSPE and some possessed mPEG2000-HZ-PE. The solvent was then evaporated using a rotary evaporator to produce a thin lipid film. Before hydration, the lipid film was flushed with nitrogen. Liposomes were formed by hydration of the lipid film with maltose solution in HEPES buffer as hydrophilic phase and were heated. The resulting multilamellar vesicles (MLVs) were then downsized, by extrusion through stacked polycarbonate filters with a mini-extruder apparatus. The stacked polycarbonate filters were stacked 200 and 100 nm polycarbonate filters. The particle size (Z-average), charge (Zeta potential), and poly dispersity index (PDI) of the liposomes were determined by a particle size analyzer.

Example 4

Physicochemical Characterization

In this example, the physicochemical characterization was carried out for the prepared empty liposomes and silibinin-loaded liposomes, the synthesizing of which are described in more detail in connection with Example 2 and Example 3.

Physicochemical Characterization of Empty Liposomes

The mean particle diameters, PDI, and Zata potential of mPEG2000-HZ-PE and mPEG2000-DSPE liposomes are presented and set forth in TABLE 1. As seen from Table 1, there was no significant difference in Z-average of different liposomal formulations (p>0.05).

TABLE 1

Physical properties of empty mPEG2000-DSPE and mPEG2000-HZ-PE molecules.

| Liposomal formulations | Z-average size (nm)[a] | PDI | Zeta potential (mV) |
|---|---|---|---|
| Empty mPEG2000-DSPE Liposomes | 114 ± 0.41 | 0.154 ± 0.008 | −26.7 |
| Empty mPEG2000-Hz-PE Liposomes | 118.2 ± 0.85 | 0.162 ± 0.023 | −27.7 |

[a] Mean ± SD (n = 3).

Physical Properties of mPEG2000-DSPE and mPEG2000-HZ-PE Liposomes Containing Silibinin.

The mean particle diameters of the resulting mPEG2000-HZ-PE and mPEG2000-DSPE liposomes, as well as their PDI, and Zata potential are presented and set forth in TABLE 2 herein below. As shown in TABLE 2, the mPEG2000-HZ liposomes had higher Z-Average size, but no significant difference was observed in Zeta potential.

TABLE 2

Physical properties of empty mPEG2000-DSPE and mPEG2000-HZ-PE liposomes

| Liposomal formulations | Z-average size (nm)[a] | PDI | Zeta potential (mV) |
|---|---|---|---|
| Silibinin containing mPEG2000-HZ-PE | 143 ± 3.5 | 0.132 ± 0.027 | −15.2 |
| Silibinin containing mPEG2000-DSPE | 103.05 ± 2.05 | 0.190 ± 0.023 | −15 |

[a] Mean ± standard deviation (n = 3).

Example 4

Cell Viability Assay

In this example, the cell viability was determined using methyl thiazolyl tetrazolium (MTT) suspension to each well of a 96-well cell culture plate. Each plate included negative control wells with medium and no cells. After overnight incubation of plates at 37° C., 5% CO2, the medium was carefully aspirated off, avoiding the removal of cells, and replaced with fresh medium (200 µl) containing up to 100 µl of formulations. The plates were incubated at 37° C., 5% CO2 for 24, 48 and 72 hours. Four hours before the end of incubation, the medium was carefully aspirated off and replaced by 100 µl FCS free cell cultured medium containing 10 µl of MTT solution. Associated with living cells in the FCS free cell cultured medium, mitochondrial dehydrogenases converted soluble MTT yellow dye to an insoluble purple formazan precipitate by cleavage of the tetrazolium ring. The conversion was used to develop an assay system for measurement of cell viability.

Continuing with description of Example 4, produced insoluble formazan was dissolved by adding 200 µl Dimethyl sulfoxide (DMSO) and its optical density (OD) was read with a multi-well scanning spectrophotometer at a wavelength of 570 nano meters 4T1 cell cultured wells containing 200 µl Roswell Park Memorial Institute (RPMI) cell culture medium are used as the positive control in each plate.

The percentage of cytotoxicity was calculated according to Eqns. (1)-(3) below $$\% \text{ Cytotoxicity} = 100 \times (1 - A) \qquad \text{Eqn. (1)}$$

$$A = \left( \frac{\text{mean absorbance drug treated cells} - \text{mean absorbance negative control}}{\text{mean absorbance positive control cells} - \text{mean absorbance negative control}} \right) \qquad \text{Eqn. (2)}$$

$$\% \text{ Viability} = 100 - \% \text{ Cytotoxicity} \qquad \text{Eqn. (3)}$$

Example 5

In-Vitro Study
In-Vitro Cytotoxicity of Polyethylene Glycol-Phospholipid Conjugated Molecules The tumor cell specific cytotoxicity effects of prepared polyethylene glycol-phospholipid conjugated molecules (mPEG2000-HZ-PE) were measured on 4T1 cancer cells. The tumor-specific cytotoxicity effects of the mPEG2000-HZ-PE conjugated molecules were then compared with mPEG2000-DSPE conjugated molecules having properties and uses in preparing the liposome compositions that would be known to those skilled in the art. The mPEG2000-HZ-PE conjugated molecules showed tumor-specific cytotoxic effects, as can be seen in TABLE 3 below, that compares to a result of half maximal inhibitory concentration (IC50).

TABLE 3

Tumor-specific cytotoxicity of mpeg- Hz-PE conjugates during different incubation period against 4T1 cancer cells.

| Conjugates | Time (Hours) | IC50 µg/ml | IC50 µM |
|---|---|---|---|
| mpeg Hz PE conjugate | 24 h | 39.96 ± 11.2 | 12 ± 3.36 |
| | 48 h | 1.94 ± 0.85 | 0.58 ± 0.25 |
| | 72 h | 1.37 ± 0.56 | 0.41 ± 0.16 |
| mpeg DSPE conjugate | 24 h | There was no significant cytotoxicity | |
| | 48 h | | |
| | 72 h | | |

In-Vitro Cytotoxicity of Empty mPEG2000-HZ-PE and mPEG2000-DSPE Liposomes

In this example, the time-dependent, tumor-specific cytotoxicities of the prepared empty mPEG2000-HZ-PE liposome and the mPEG2000-DSPE liposomes were measured on 4T1 cancer cells. As shown in TABLE 4 herein below, there were significant differences in the half maximal inhibitory concentration (IC50) of mPEG2000-HZ-PE and mPEG2000-DSPE during the incubation period.

TABLE 4

Tumor cell specific cytotoxicity of empty mPEG2000-HZ-PE and mPEG2000-DSPE liposomes in different incubation period against 4T1 cancer cells.

| Liposomal formulations | Time (Hours) | IC50 µg/ml | IC50 µM |
|---|---|---|---|
| Empty mpeg Hz PE Liposomes | 24 h | 83.87 ± 23.13 | 25 ± 6.9 |
| | 48 h | 24.52 ± 6.73 | 7.33 ± 2 |
| | 72 h | 14.25 ± 4.9 | 4.26 ± 1.46 |
| Empty mpeg DSPE Liposomes | 24 h | There was no significant cytotoxicity | |
| | 48 h | | |
| | 72 h | | |

In-Vitro Cytotoxicity of Silibinin Containing mPEG2000-HZ-PE and mPEG2000-DSPE Liposomes The time-dependent tumor-specific cytotoxicity of mPEG2000-HZ-PE and mPEG2000-DSPE liposomes loading by silibinin, were measured on 4T1 cancer cells. The results are presented in TABLE 5 herein below. It can be understood from data summarized TABLE 5 that there are significant differences in the half maximal inhibitory concentration (IC50) of silibinin containing mPEG2000-HZ-PE and silibinin containing mPEG2000-DSPE liposomes during the incubation period.

TABLE 5

Tumor-specific cytotoxicity of mPEG2000-HZ-PE and mPEG2000-DSPE liposomes loading by silibinin during different incubation period against 4T1 cancer cells.

| Liposomal formulations | Time (Hours) | IC50 µg/ml | IC50 µM |
|---|---|---|---|
| Silibinin containing mPEG2000-Hz-PE Liposomes | 24 h | 123 ± 16.3 | 254.9 ± 33.8 |
| | 48 h | 16.34 ± 8.9* | 33.86 ± 18.4 |
| | 72 h | 6.72 ± 3.9** | 13.92 ± 8.1 |
| Silibinin containing mPEG2000-DSPE Liposomes | 24 h | 138.51 ± 75.9 | 287.1 ± 157.3 |
| | 48 h | 46.63 ± 6.3 | 96.65 ± 13.05 |
| | 72 h | 28.36 ± 7.9 | 58.78 ± 16.37 |

*Significant statistic difference (P < 0.01) between mPEG2000 Hz-PE and mPEG2000-DSPE silibinin-loaded liposomes.
**Significant statistic difference (P < 0.02) between mPEG2000 Hz-PE and mPEG2000-DSPE silibinin-loaded liposomes.

Example 6

In Vivo Study

In this example, female BALB/c mice (aged 8 weeks, 18-20 g) are used to carry out the experiments. All animal experiments were performed in compliance with the Institutional Ethical Committee and Research Advisory Committee of Mashhad University of Medical Sciences guidelines (Education Office, dated Feb. 26, 2008; proposal code 87848). The mice are kept in an animal house of Mashhad Avecina Research Center at 21° C. in a colony room 12/12 h light/dark cycle with free access to water and food. All mice received humane care in compliance with institutional guidelines. On day 0, BALB/c mice were given subcutaneous injections of 4T1 cells ($2.5 \times 10^5$ cells per mouse) in the right hind flank. Then tumors were allowed to grow until mice had palpable tumors (11 days), and animals were divided into 3 different treatment groups with 5-6 mice per each group.

The silibinin containing liposomal composition of prepared PEG-conjugates, which were prepared pursuant to the teachings of the present application, were injected via the lateral tail vein at 45 mg/kg mPEG2000-HZ-PE and 7 mg/kg silibinin. Starting on the day of the treatment, the animals' weight, tumor volume and overall health were monitored on 3 occasions a week for 75 days. Three dimensions of tumor were measured with calipers and tumor volume was calculated via the following Eqn. (4):

$$\text{Tumor volume} = (\text{height} \times \text{length} \times \text{width}) \times 0.52 \text{ cm}^3 \qquad \text{Eqn. (4)}$$

For ethical considerations, mice were sacrificed due to a decrease in their body weight (>15% loss) or tumor enlargement (more than 2 cm in one dimension) or declining health. Mouse survival was analyzed with GraphPad Prism version 5 (GraphPad software, San Diego, Calif.). The time to reach end point (TTE) for each mouse was calculated from the equation of the line obtained by exponential regression of the tumor growth curve. Subsequently, the percent of tumor growth delay (% TGD) was calculated, as shown by Eqn. (5) that follows based on the difference between the mean TTE of treatment group (T) and the mean TTE of the control group (C).

$$\% \text{ TGD} = [(T-C)/C] \times 100 \qquad \text{Eqn. 5}$$

Referring now to FIG. 1 of the DRAWINGS, the anti-tumor efficiency of silibinin-loaded mPEG2000-HZ-PE liposomes regarding to the treated animals, is significantly higher than the silibinin-loaded mPEG2000-DSPE liposomes. The same efficiency was obtained after 55 days for the silibinin-loaded mPEG2000-DSPE liposomes.

Figure 2:
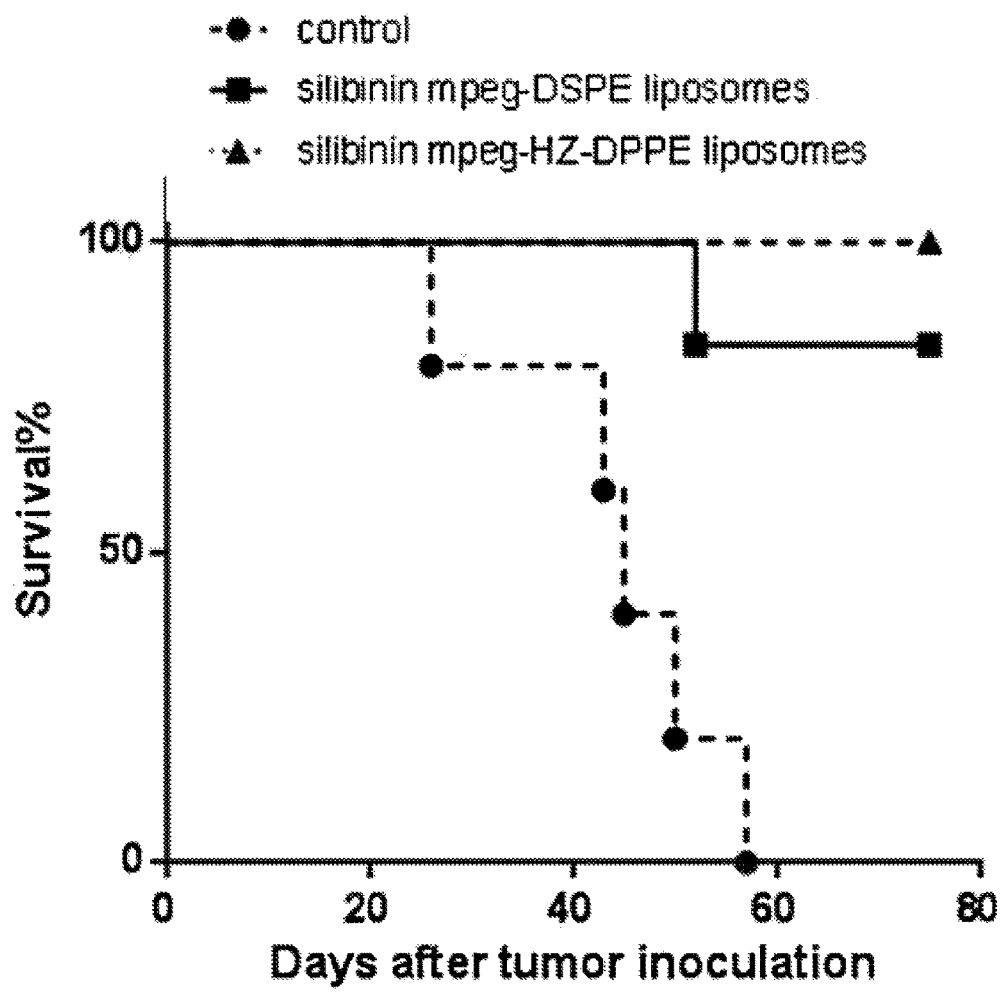
FIG. 2. Illustrates the result of in vivo survival test in female BALB/c mice bearing 4T1 breast tumor treated by mPEG HZ PE liposomal formulations according to one or more aspects of this disclosure.

The results of in vivo survival experiments on treated mice are shown in FIG. 2 of the DRAWINGS and presented in TABLE 6 herein below. With reference now to FIG. 2, this figure illustrates when silibinin-loaded mPEG2000-HZ-PE liposomes are used, the survival percent of the cells is almost 75% on day 35, while the same survival percent in the case of silibinin-loaded mPEG2000-DSPE is obtained on day 55 after intravenous administration.

Data summarized in TABLE 6 herein below shows some criteria concerning the therapeutic efficacy of liposomal formulations in mouse model. The data presented in this table include median survival time, time to reach endpoint (TTE) and the percentage of tumor growth delay (% TGD). It can be understood from data summarized in TABLE 6 that the mPEG2000-HZ-PE Liposomes loaded by silibinin had higher effects to retard the growth of tumors and therefore are better to increase the median survival time.

TABLE 6

Therapeutic efficacy data of silibinin mPEG2000-HZ-PE and silibinin mpeg-DSPE liposomal compositions in mice bearing 4T1 tumor.

| Group | MST [a] (day) | TTE [b] (Day ± SD) | TGD [c] (%) |
|---|---|---|---|
| Control | 45 | 44.2 ± 11.51 | — |
| Silibinin mpeg 2000-HZ-PE Liposomes | Undifined | 75 (tumor free) | 66.66 |
| Silibnin mPEG2000-DSPE Liposomes | Undifined | 71.16 ± 9.38 | 30.66 |

[a] Median survival time.
[b] Time to reach end point.
[c] Tumor growth delay.

It will be understood that the terms and expressions used herein have the ordinary meaning as is accorded to such terms and expressions with respect to their corresponding respective areas of inquiry and study, except where specific meanings have otherwise been set forth herein. Relational terms such as first and second and the like may be used solely to distinguish one entity or action from another without necessarily requiring or implying any actual such relationship or order between such entities or actions. The terms "comprises," "comprising," and any other variation thereof, are intended to cover a non-exclusive inclusion, such that a process, method, article, or apparatus that comprises a list of elements does not include only those elements but may include other elements not expressly listed or inherent to such process, method, article, or apparatus. An element proceeded by "a" or "an" does not, without further constraints, preclude the existence of additional identical elements in the process, method, article, or apparatus that comprises the element.

While the present application has been illustrated by the description of the examples thereof, and while the example have been described in detail, it is not the intention of the applicant to restrict or in any way limit the scope of the appended claims to such detail. Additional advantages and modifications will readily appear to those skilled in the art. Therefore, the application in its broader aspects is not limited to the specific details, representative apparatus and method, and illustrative examples shown and described. Accordingly, departures may be made from such details without departure from the breadth or scope of the applicant's concept. Furthermore, although the present application has been described in connection with a number of exemplary embodiments and implementations, the present application is not so limited but rather covers various modifications and equivalent arrangements, which fall within the purview of the appended claims.

What is claimed is:

1. A liposomal composition for treatment of cancer, comprising:
    at least one polyethylene glycol (PEG)-phospholipid conjugated molecule;
    a cholesterol; and
    at least one phospholipid, wherein:
    the at least one (PEG)-phospholipid conjugated molecule comprises a methoxypolyethylene glycol (mPEG)-2000-hydrazide (HZ)-polyethylene (PE) conjugated molecule, and
    the at least one phospholipid is selected from the group consisting of dipalmitoylphosphatidylcholine (DPPC), dimyristoylphosphatidylcholine (DMPC), dipalmitoyl-phosphatidylethanolamine, and combinations thereof.

2. The liposomal composition according to claim 1, wherein the at least one mPEG-2000-HZ-PE conjugated molecule is a tumor cell specific cytotoxic agent.

3. The liposomal composition according to claim 1, wherein a molar percent of the at least one mPEG-2000-HZ-PE conjugated molecule in the liposomal composition ranges from about 3 to about 6 percent.

4. The liposomal composition according to claim 1, wherein a molar ratio of phospholipid:cholesterol:mPEG-2000-HZ-PE conjugated molecule ranges from about 20:3:1 to about 22:6:2.

5. A liposome composition for treatment of cancer, comprising:
an anticancer drug;
at least one methoxypolyethylene glycol (mPEG)-2000-hydrazide (HZ)-polyethylene (PE) conjugated molecule;
a cholesterol; and
at least one phospholipid,
wherein the at least one phospholipid is selected from the group consisting of dipalmitoylphosphatidylcholine (DPPC), dimyristoylphosphatidylcholine (DMPC), dipalmitoylphosphatidylethanolamine, and combinations thereof.

6. The liposome composition according to claim 5, wherein the anticancer drug is selected from the group consisting of herbal drugs and chemotherapeutic agents.

7. The liposome composition according to claim 5, wherein the anticancer drug is selected from the group consisting of Epigallocatechin-3-gallate (EGCG), soy isoflavones, Isoflavones genistein, daidzein, Coumarins, flavonoids, silibinin, polyphenols, baicalin, lycopenes, Vincristine, doxorubicin, cisplatin, 5-fluorouracil, Methotrexate, Cyclophosphamide, mustine, prednisolone, epirubicin, folinic acid, oxaliplatin, etoposide, and bleomycin.

8. The liposomal composition according to claim 5, wherein the at least one mPEG-2000-HZ-PE conjugated molecule is a tumor cell specific cytotoxic agent.

9. The liposome composition according to claim 5, wherein a molar percent of the at least one mPEG-2000-HZ-PE conjugated molecule in the liposome composition ranges from about 3 to about 6 percent.

10. The liposome composition according to claim 5, wherein a molar ratio of phospholipid:cholesterol:anticancer drug:mPEG-2000-HZ-PE conjugated molecule ranges from about 20:5:3:1 to about 22:6:6:2.

11. The liposome composition according to claim 5, wherein the anticancer drug comprises silibinin.

12. The liposome composition according to claim 5, wherein a molar ratio of phospholipid:cholesterol:mPEG-2000-HZ-PE conjugated molecule ranges from about 20:3:1 to about 22:6:2.

13. A liposome composition for treatment of cancer, comprising:
an anticancer drug;
at least one methoxypolyethylene glycol (mPEG)-2000-hydrazide (HZ)-polyethylene (PE) conjugated molecule;
a cholesterol; and
at least one phospholipid,
wherein a molar ratio of phospholipid:cholesterol:anticancer drug:mPEG-2000-HZ-PE conjugated molecule ranges from about 20:5:3:1 to about 22:6:6:2.

14. The liposome composition according to claim 13, wherein the anticancer drug is silibinin.

15. The liposome composition according to claim 13, wherein the at least one phospholipid is selected from the group consisting of egg yolk phosphatidylcholine (EPC), soybean phosphatidylcholine, dipalmitoylphosphatidylcholine (DPPC), dimyristoylphosphatidylcholine (DMPC), distearoylphosphatidylcholine (DSPC), dioleoylphosphatidylcholine (DOPC) egg yolk phosphatidylethanolamine, dipalmitoylphosphatidylethanolamine, and combinations thereof.

16. The liposome composition according to claim 13, wherein the at least one anticancer drug is selected from the group consisting of Epigallocatechin-3-gallate (EGCG), soy isoflavones, Isoflavones genistein, daidzein, Coumarins, flavonoids, silibinin, polyphenols, baicalin, lycopenes, Vincristine, doxorubicin, cisplatin, 5-fluorouracil, Methotrexate, Cyclophosphamide, mustine, prednisolone, epirubicin, folinic acid, oxaliplatin, etoposide, bleomycin, and combinations thereof.

17. The liposome composition according to claim 13, wherein a molar percent of the at least one mPEG-2000-HZ-PE conjugated molecule in the liposome composition ranges from about 3 to about 6 percent.

* * * * *